US011873301B2

(12) United States Patent
Redline et al.

(10) Patent No.: US 11,873,301 B2
(45) Date of Patent: Jan. 16, 2024

(54) CROSSLINKED POLYMERS WITH TUNABLE COEFFICIENTS OF THERMAL EXPANSION

(71) Applicant: National Technology & Engineering Solutions of Sandia, LLC, Albuquerque, NM (US)

(72) Inventors: Erica M. Redline, Albuquerque, NM (US); Chad L. Staiger, Albuquerque, NM (US); David R. Wheeler, Albuquerque, NM (US); Leah N. Appelhans, Tijeras, NM (US); Jeffrey C. Foster, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 18/123,665

(22) Filed: Mar. 20, 2023

(65) Prior Publication Data
US 2023/0250099 A1   Aug. 10, 2023

Related U.S. Application Data

(62) Division of application No. 17/344,717, filed on Jun. 10, 2021, now Pat. No. 11,739,092.
(Continued)

(51) Int. Cl.
*C07D 471/14* (2006.01)
*C08K 5/17* (2006.01)
(Continued)

(52) U.S. Cl.
CPC .......... *C07D 471/14* (2013.01); *C07C 13/547* (2013.01); *C07C 211/60* (2013.01);
(Continued)

(58) Field of Classification Search
CPC .............. C07C 13/547; C07C 2603/30; C07C 2603/36; C07C 211/60; C07C 211/61
See application file for complete search history.

(56) References Cited

U.S. PATENT DOCUMENTS

| | | | |
|---|---|---|---|
| 10,723,834 B1 * | 7/2020 | Davis | C08G 63/547 |
| 2016/0096932 A1 | 4/2016 | Pugh et al. | |
| 2021/0102066 A1 | 4/2021 | Lu et al. | |

FOREIGN PATENT DOCUMENTS

| | | |
|---|---|---|
| CN | 107163246 A | 9/2017 |
| CN | 110194836 A | 9/2019 |

(Continued)

OTHER PUBLICATIONS

Mathisen (Dye Labeling Technique for Monitoring the Cure of Polyimides and Polyureas: Model Compound Studies, Macromolecules, 1987, 20, pp. 1414-1416).*
(Continued)

*Primary Examiner* — Brieann R Johnston
(74) *Attorney, Agent, or Firm* — Kevin. W. Bieg

(57) ABSTRACT

Curatives and their resulting thermosets and other crosslinked polymers can reduce thermal expansion mismatch between an encapsulant and objects that are encapsulated. This can be accomplished by incorporating a negative CTE moiety into the thermoset resin or polymer backbone. The negative CTE moiety can be a thermal contractile unit that shrinks as a result of thermally induced conversion from a twist-boat to chair or cis/trans isomerization upon heating. Beyond CTE matching, other potential uses for these crosslinked polymers and thermosets include passive energy generation, energy absorption at high strain rates, mechanophores, actuators, and piezoelectric applications.

3 Claims, 12 Drawing Sheets

Related U.S. Application Data

(60) Provisional application No. 63/039,126, filed on Jun. 15, 2020.

(51) Int. Cl.
| | |
|---|---|
| *C08K 5/053* | (2006.01) |
| *C07C 211/60* | (2006.01) |
| *C07D 321/12* | (2006.01) |
| *C08K 5/23* | (2006.01) |
| *C07C 13/547* | (2006.01) |

(52) U.S. Cl.
CPC ............ *C07D 321/12* (2013.01); *C08K 5/053* (2013.01); *C08K 5/17* (2013.01); *C08K 5/235* (2013.01); *C07C 2602/12* (2017.05); *C07C 2603/30* (2017.05); *C07C 2603/36* (2017.05)

(56) References Cited

FOREIGN PATENT DOCUMENTS

| CN | 114507335 A | 5/2022 |
|---|---|---|
| WO | 2019195442 A1 | 10/2019 |

OTHER PUBLICATIONS

Chun, H. et al., "Preparation of Ultra-Low CTE Epoxy Composite Using the New Alkoxysilyl-Functionalized Bisphenol A Epoxy Resin," Polymer, 2018, vol. 135, pp. 241-250.

Tada, H. et al., "Thermal Expansion Coefficient of Polycrystalline Silicon and Silicon Dioxide Thin Films at High Temperatures," Journal of Applied Physics, 2000, vol. 87, pp. 4189-4193.

Yates, B. et al., "Thermal Expansion at Elevated Temperatures: II. Aluminium Oxide: Experimental Data between 100 and 800 K and Their Analysis," Journal of Physics C: Solid State Phys., 1972, vol. 5, pp. 1046-1058.

Miller, W. et al., "Negative Thermal Expansion: A Review," Journal of Materials Science, 2009, vol. 44, pp. 5441-5451.

Takenaka, K., "Progress of Research in Negative Thermal Expansion Materials: Paradigm Shift in the Control of Thermal Expansion," Frontiers in Chemistry, 2018, vol. 6, Article 267, 13 pages.

Shen, X. et al., "Large Negative Thermal Expansion of a Polymer Driven by a Submolecular Conformational Change," Nature Chemistry, 2013, vol. 5, pp. 1035-1041.

Wang, Z. et al., "Design and Synthesis of Thermal Contracting Polymer with Unique Eight-Membered Carbocycle Unit," Macromolecules, 2018, vol. 51. pp. 1377-1385.

Fu, W. et al., "Arene Substitution Design for Controlled Conformational Changes of Dibenzocycloocta-1,5-dienes," Journal of the American Chemical Society, 2020, vol. 142, pp. 16651-16660.

Franck, G. et al., "Working with Hazardous Chemicals," Organic Syntheses, 2012, vol. 89, pp. 55-65.

Giumanini, A.G. et al., "Nitration of Diphenylmethane and the Isometric Nitrodiphenylmethanes in Dichloromethane," Industrial and Engineering Chemistry Research, 2002, vol. 41, pp. 1929-1934.

Tillet, G. et al., "Crosslinking of Fluoroelastomers by "Click" Azide-Nitrile Cycloaddition," Journal of Polymer Science Polymer Chemistry, 2015, vol. 53, pp. 1171-1173.

Jin, K. et al., "Soluble, Thermally Stable, and Low Thermal Expansion Polyarylamides Enabled by a Seven-Membered Carbocycle," ACS Appl. Plym. Meter. (2020) 2:5423-5431.

\* cited by examiner

CROSSLINKED POLYMERS WITH TUNABLE COEFFICIENTS OF THERMAL EXPANSION

CROSS-REFERENCE TO RELATED APPLICATIONS

This application is a divisional of application Ser. No. 17/344,717, filed Jun. 10, 2021, which claims the benefit of U.S. Provisional Application No. 63/039,126, filed Jun. 15, 2020, both of which are incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to crosslinked polymers and, in particular, to thermosets and other crosslinked polymers with tunable coefficients of thermal expansion.

BACKGROUND OF THE INVENTION

Thermoset polymers are low weight, low cost, high performance materials with excellent chemical, thermal, and mechanical stability. See J.-P. Pascault et al., *Thermosetting Polymers*, CRC Press: New York, 2002; *Cross-Linked Polymers: Chemistry, Properties, and Applications*, American Chemical Society: Washington, D.C., 1988, Vol. 367; and W. Brostow et al., Chapter 8 — Epoxies, In *Handbook of Thermoset Plastics (Third Edition)*, Dodiuk, H.; Goodman, S. H., Eds. William Andrew Publishing: Boston, 2014; pp 191-252. In addition to their use in homogenous components, thermoset polymers are frequently employed in combination with other materials, acting as adhesives, encapsulants, composite matrices, or barriers. See T. Engels, Chapter 10—Thermoset adhesives, In *Thermosets (Second Edition)*, Guo, Q., Ed. Elsevier: 2018; pp 341-368; F. Aguirre-Vargas, Chapter 11—Thermoset coatings, In *Thermosets (Second Edition)*, Guo, Q., Ed. Elsevier: 2018; pp 369-400; E. Aksu, Chapter 14—Thermosets for pipeline corrosion protection, In *Thermosets (Second Edition)*, Guo, Q., Ed. Elsevier: 2018; pp 453-476; S. Agarwal and R. K. Gupta, Chapter 8—The use of thermosets in the building and construction industry, In *Thermosets (Second Edition)*, Guo, Q., Ed. Elsevier: 2018; pp 279-302; I. Hamerton and J. Kratz, Chapter 9—The use of thermosets in modern aerospace applications, In *Thermosets (Second Edition)*, Guo, Q., Ed. Elsevier: 2018; pp 303-340; M. Biron, Chapter 6—Composites, In *Thermosets and Composites (Second Edition)*, Biron, M., Ed. William Andrew Publishing: Oxford, 2013; pp 299-473; A. Fangareggi and L. Bertucelli, Chapter 12—Thermoset insulation systems, In *Thermosets (Second Edition)*, Guo, Q., Ed. Elsevier: 2018; pp 401-438; and K. Netting, Chapter 13—Thermosets for electric applications, In *Thermosets (Second Edition)*, Guo, Q., Ed. Elsevier: 2018; pp 439-452. In these cases, additional practical constraints are imposed upon the resulting composite materials, including the need to closely match the thermal expansion behaviors of the various constituents to achieve optimal performance.

Most solid materials experience positive thermal expansion upon heating, and the degree and rate at which this expansion occurs is referred to as the coefficient of thermal expansion (CTE). Bulk polymers typically possess large, positive CTEs in comparison to other materials. For example, a representative CTE value of a cured epoxy is ~55 ppm/° C., whereas common inorganic fillers such as silica or alumina possess CTE values of ~6 ppm/° C. and ~8 ppm/° C., respectively. See H. Chun et al., *Polymer* 135, 241 (2018); H. Tada et al., *J. Appl. Phys.* 87(9), 4189 (2000); and B. Yates et al., *J. Phys. C* 5(10), 1046 (1972). In composites or devices, large differences in CTE between materials leads to CTE mismatch, causing internal thermomechanical stresses that ultimately reduce reliability, the service life of the component and, in some cases, result in catastrophic device failure. See J. H. Okura et al., *Microelectron. Reliab.* 40, 1173 (2000); and J. de Vreugd et al., *Microelectron. Reliab.* 50, 910 (2010). Fluoroelastomers and rubbers used in high temperature applications, such as seals for geothermal, oil, and gas applications, can also suffer from CTE issues. As such, fine-tuning of polymer CTE represents a significant scientific challenge of interest to a variety of industries.

One strategy to address CTE mismatch is to incorporate negative thermal expansion (NTE) materials as fillers within the polymer matrix. See W. Miller et al., *J. Mater. Sci.* 44(20), 5441 (2009); and K. Takenaka, *Front. Chem.* 6, 267 (2018). Such fillers act to depress the overall CTE of the composite. Inorganic compounds such as $ZrW_2O_8$ (CTE ~−9 ppm/° C.), or $GaNMn_3$ (CTEs as low as −70 ppm/° C.), have been explored for this purpose, allowing for the CTE of their respective composites to be modulated over an order of magnitude depending on filler loading. See L. A. Neely et al., *J. Mater. Sci.* 49(1), 392 (2014); P. Badrinarayanan et al., *Macromol. Mater. Eng.* 298(2), 136 (2013); H. Wu et al., *ACS Appl. Mater. Interfaces* 5(19), 9478 (2013); L. M. Sullivan and C. M. Lukehart, *Chem. Mater.* 17(8), 2136 (2005); and J. Lin et al., *Compos. Sci. Technol.* 146, 177 (2017). However, despite their promise, such composite materials are typically limited in their useful CTE window to sub-ambient temperatures. Moreover, high loadings of inorganic fillers are often required (80-90 wt %) to significantly reduce CTE values, which can hinder material processing and dramatically alter morphology and mechanical performance.

Therefore, there is a need for thermoset and other crosslinked polymer systems that eliminate the need for fillers while achieving the CTE of a filled thermoset. In particular, there is a need for filler-less thermosets that achieve CTE tunability to near zero ppm/° C.

SUMMARY OF THE INVENTION

The present invention is directed to thermoset and other crosslinked systems to reduce thermal expansion mismatch between an encapsulant and objects that are encapsulated. In one aspect, the invention is directed to curatives comprising thermally contractile units that undergo a reversible twist-boat to chair isomerization upon heating accompanied by a change in molecular volume. For example, the curative can comprise a disubstituted-dibenzocyclooctane, disubstituted-dibenzocycloheptane, disubstituted-stilbene, or disubstituted-azobenzene. For example, the disubstitution can comprise a diamine, dicarboxylic acid, dialcohol, diisocyanate, dianhydride, diazido, or diepoxide substitution. Exemplary curatives include diamino-dibenzocyclooctane, diazido-dibenzocyclooctane, diepoxide-dibenzocyclooctane, diazido-dibenzocyclooctane, dihydroxy-dibenzocyclooctane, diisocyanate-dibenzocyclooctane, dicarboxylic acid-substituted-dibenzocyclooctane, dianhydride-dibenzocyclooctane, diamino-dibenzocycloheptane, diamino-stilbene, and diamino-azobenzene.

As an example of the invention, diamino curatives based on the thermally-isomerizable dibenzocyclooctane (DBCO) motif were synthesized. Density-functional theory (DFT) calculations on model compounds revealed a temperature-dependent isomerization equilibrium that was most significant for the cis-diamino-DBCO (DADBCO) regioisomer. These novel curatives were used to prepare epoxy/amine thermosets. Consistent with the DFT data, an epoxy cured with cis-DADBCO possessed a low CTE value of 20 ppm/° C. below its $T_g$ and contracted massively above $T_g$, amounting to a net contraction of the material over the tested temperature range that was highly reversible. These and related compounds can be readily incorporated into a wide range of materials to fine tune CTE values.

BRIEF DESCRIPTION OF THE DRAWINGS

The detailed description will refer to the following drawings, wherein like elements are referred to by like numbers.

DETAILED DESCRIPTION OF THE INVENTION

Figure 1:
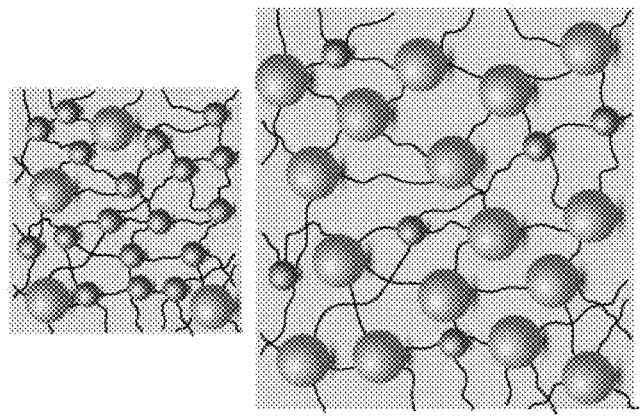
FIG. 1 is a schematic illustration of thermally controlled isomerization of DBCO between twist-boat and chair conformers and how the incorporation of such contractile units into thermoset materials influences their thermal expansion and contraction behavior.
Figure 1:
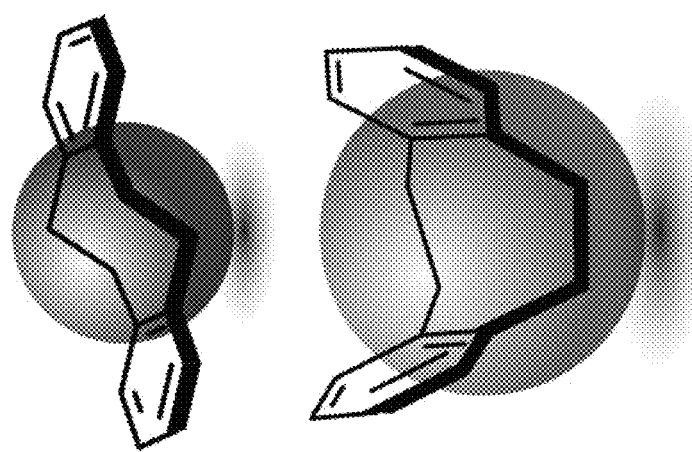

As illustrated in FIG. 1, a strategy to manipulate the CTE of thermosets involves covalent incorporation of thermally contractile units within a polymer network. See X. Shen et al., *Nat. Chem.* 5(12), 1035 (2013). These "shrinking" linkages oppose thermal expansion during heating, with the net effect of reducing the CTE of the material to near or less than zero in some cases. As shown in the figure, one such contractile group is DBCO, comprising a flexible cyclooctane ring connecting two rigid phenyl groups which undergoes a reversible twist-boat to chair isomerization upon heating accompanied by a decrease in molecular volume. See X. Shen et al., *Nat. Chem.* 5(12), 1035 (2013); Z. Wang et al., *Macromolecules* 51(4), 1377 (2018); and W. Fu et al., *J. Am. Chem. Soc.* 142(39), 16651 (2020). To date, DBCO has been incorporated into polyarylamide thermoplastics and thermosets but has yet to be explored in other polymer systems.

An exemplary embodiment of the present invention uses the DBCO moiety to prepare di-aniline crosslinkers for use in epoxy/amine thermosets. Accordingly, the influence of the amine substitution pattern in the phenyl groups was investigated by both DFT calculations and thermomechanical analysis (TMA). Depending on the regioisomer (or positional isomer) of DADBCO utilized as a crosslinker, epoxy thermosets can be prepared with near-zero, or in some cases negative, CTE values that feature highly reversible thermal expansion and contraction behavior. The resulting thermoset polymers can be important in the preparation of composite materials, especially in applications in which dimensional precision or minimization of thermal stresses is required.

Epoxy thermosets are typically prepared from low molecular weight, epoxide-functionalized resins and di-functional crosslinkers such as dianhydrides or diamines.

Figure 2A:
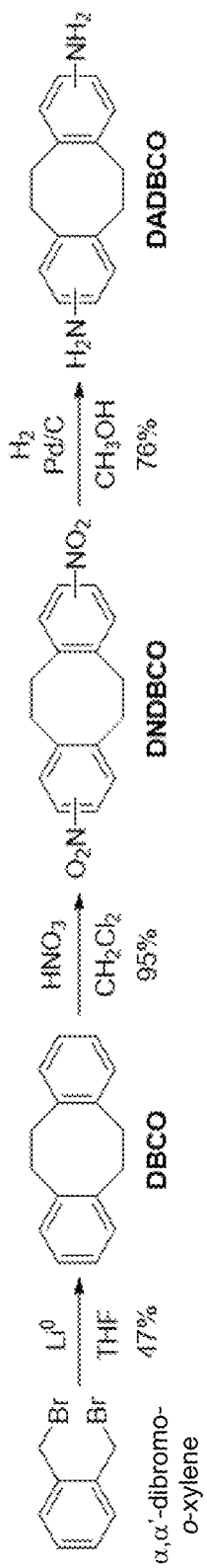
FIG. 2A shows a synthetic route to prepare DADBCO.
Figure 3:
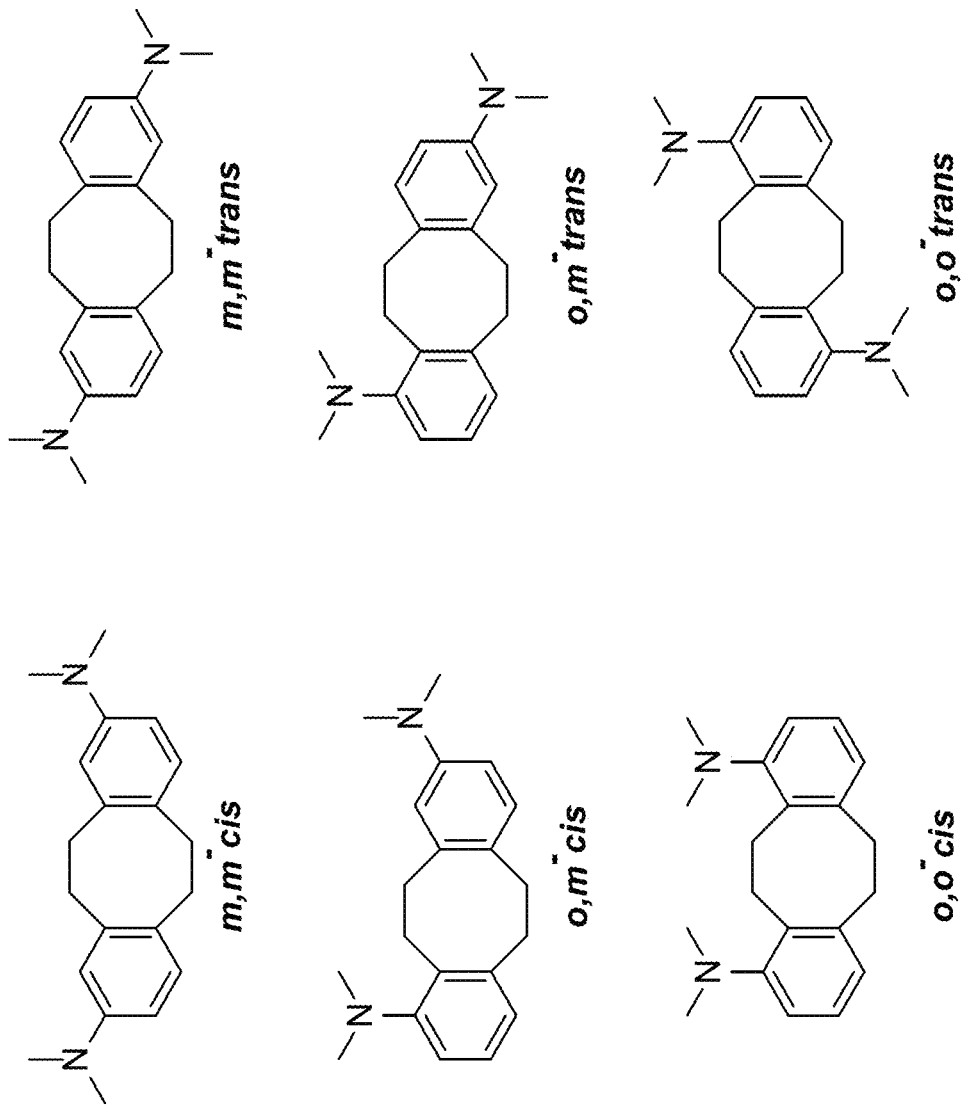
FIG. 3 shows the regioisomer structures used in DFT calculations and their abbreviations.

Epoxy/amine formulations are attractive as they can be cured at relatively low temperatures (e.g., ≤150° C.) without additional catalysts or initiators. To prepare a curative based on DBCO, a three-step synthetic approach was adopted, as shown in FIG. 2A. In the first step, α,α'-dibromo-o-xylene was dimerized in the presence of elemental Li to form a DBCO scaffold. See G. Franck et al., *Org. Syn.* 89, 55 (2012). Soft nitration of DBCO with excess $HNO_3$ in $CH_2Cl_2$ provides the dinitro derivative (DNDBCO). See A. G. Giumanini et al., *Ind. Eng. Chem. Res.* 41(8), 1929 (2002). All six of the possible regioisomers were obtained during the nitration step in approximately equal abundance (the ratio of ortho/meta nitro substituents was 2:3). In the final step, DNDBCO was hydrogenated under standard conditions to yield a mixture of DADBCO regioisomers, as shown in FIG. 3. The trans- and cis-DADBCO regioisomers can be isolated from the DADBCO isomer mixture via exhaustive chromatography.

Figure 4:
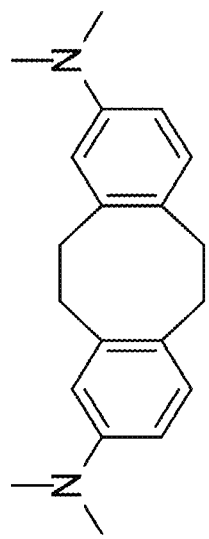
FIG. 4 is a schematic illustration of the molecular volume decrease during twist-boat to chair isomerization.
Figure 4:
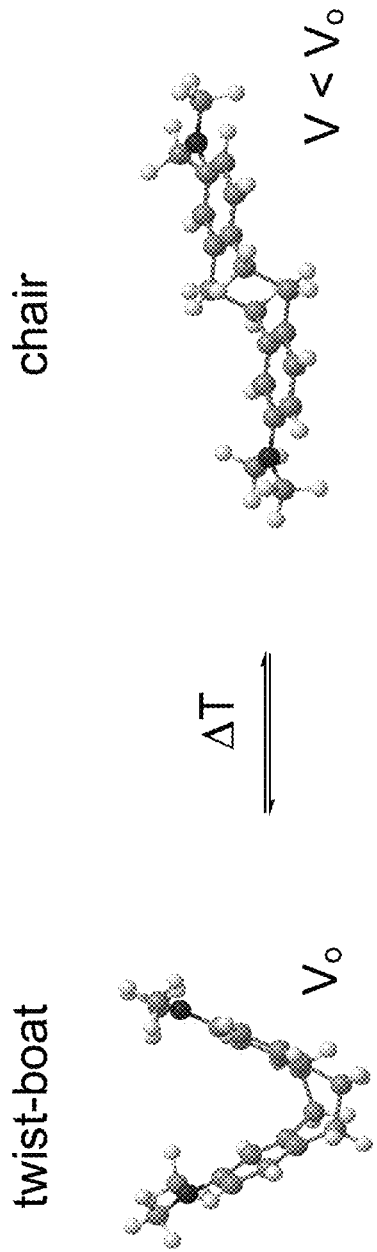
Figure 5:
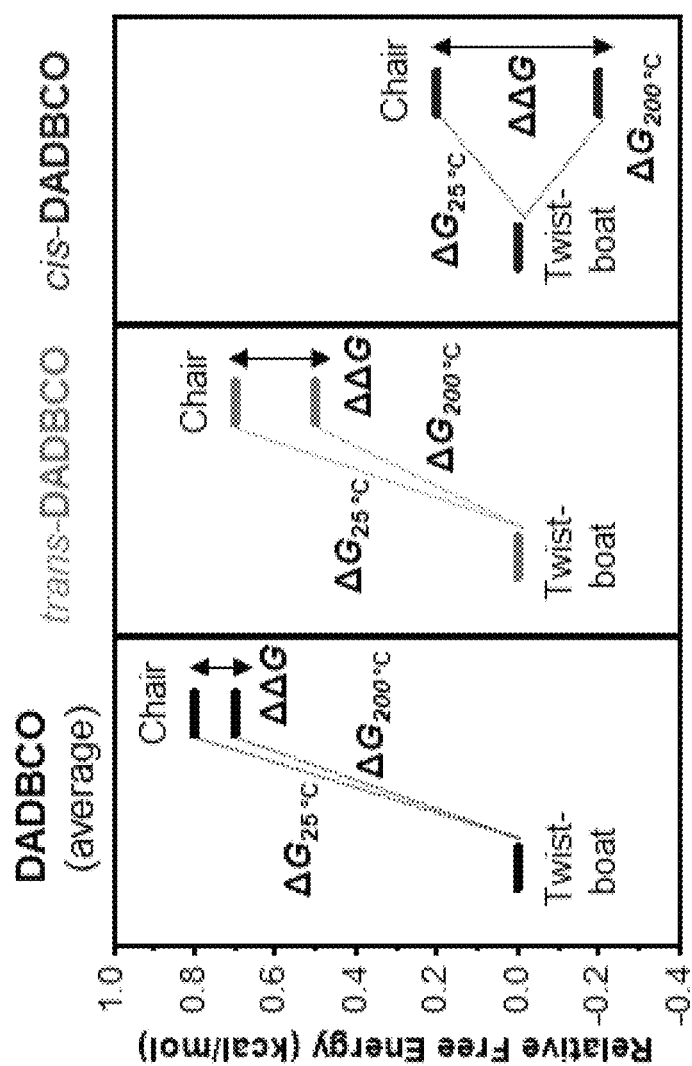
FIG. 5 is a graph of the relative free energies of the twist-boat and chair isomers at room temperature and 200° C. for the trans- and cis-DADBCO isomers compared to the averaged values from all six isomers.

The thermal isomerization of DBCO between the twist-boat and chair isomers has been thoroughly investigated using DFT calculations, X-ray crystallography, variable temperature NMR spectroscopy, and differential scanning calorimetry (DSC). See I. Alkorta and J. Elguero, *Struct. Chem.* 21(4), 885 (2010); A. Hamza, *Struct. Chem.* 21(4), 787 (2010); P. Domiano et al., *J. Chem. Soc., Perkin Trans.* 9, 1609 (1992); M. Luisa Jimeno et al., *New J. Chem.* 22(10), 1079 (1988); and W. Fu et al., *J. Am. Chem. Soc.* 142(39), 16651 (2020). However, previous studies have yet to consider the influence of regiochemistry on the isomerization equilibrium. Therefore, of interest is the influence that the amino substitution pattern has on the thermodynamics of the twist-boat to chair transition, as shown for the m,m-cis regioisomer in FIG. 4. Toward this end, DFT calculations were carried out using N,N,N',N'-tetramethylated DADBCO models for each of the six possible regioisomers shown in FIG. 3. Calculated thermodynamic parameters and molar volumes are provided in Table 1. DFT calculations on individual molecules showed that the twist-boat conformation represented the global energy minimum at room temperature regardless of amine regiochemistry, shown in FIG. 5. In addition, calculated molar volumes were lower for the chair conformer relative to twist-boat in all cases. At 200° C., $\Delta\Delta G$ ($\Delta G_{200° C.}$-$\Delta G_{25° C.}$) was negative for each compound due to the relatively higher entropy of the chair conformer. However, only the cis-regioisomer possessed negative $\Delta G_{200° C.}$ for the isomerization, indicating that the equilibrium favored the chair conformer at elevated temperature for cis-DADBCO.

TABLE 1

DFT calculations on twist-boat and chair conformers at different temperatures for the various tetramethylated DADBCO isomers. The energies, equilibrium constants, and volumes below are given in terms of chair relative to twist-boat (e.g., $\Delta H = H_{Chair} - H_{Boat}$).

| Isomer | $\Delta H_{25° C.}$ (kcal/mol) | $\Delta G_{25° C.}$ (kcal/mol) | $\Delta G_{100° C.}$ (kcal/mol) | $\Delta G_{200° C.}$ (kcal/mol) | $K_{eq, 200° C.}$ | $\Delta V^a$ (cm³/mol) |
|---|---|---|---|---|---|---|
| m,m-cis | 1.0 | 0.2 | 0.0 | −0.2 | 1.2 | −4.2 |
| m,m-trans | 1.1 | 0.7 | 0.6 | 0.5 | 0.6 | −3.6 |
| o,m-cis | 1.6 | 1.3 | 1.3 | 1.2 | 0.3 | −4.9 |
| o,m-trans | 1.4 | 1.1 | 1.1 | 1.0 | 0.3 | −3.0 |
| o,o-cis | 0.8 | 0.4 | 0.4 | 0.3 | 0.7 | −4.3 |
| o,o-trans | 1.1 | 1.1 | 1.1 | 1.0 | 0.3 | −1.7 |
| average | 1.2 | 0.8 | 0.7 | 0.5 | 0.6 | −3.6 |

[a] Molar volumes calculated from Connolly solvent-excluded molecular volumes using a 1.4 Å probe.

Figure 2B:
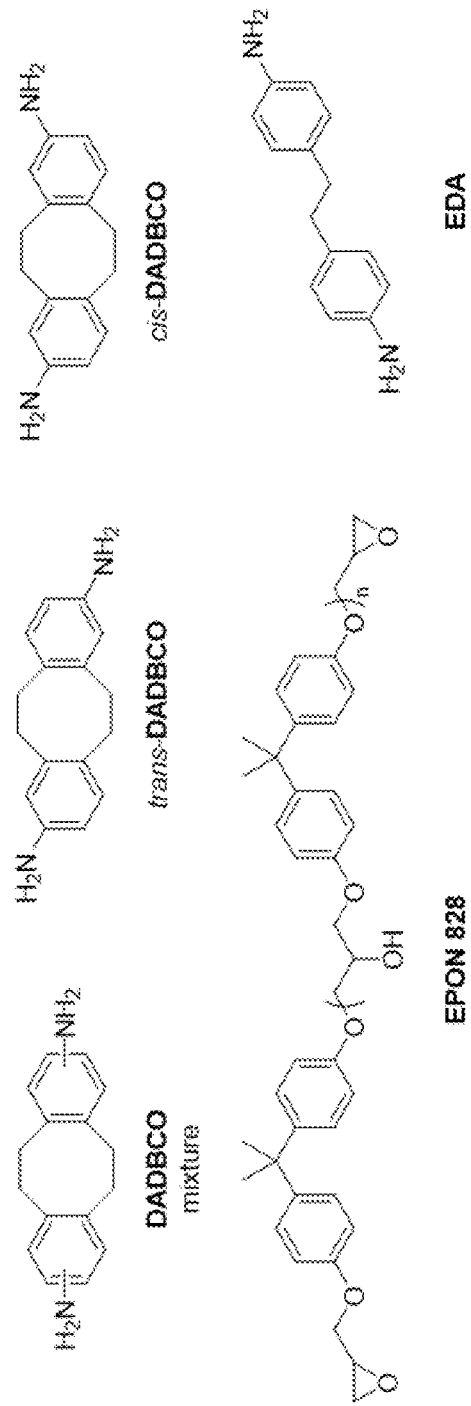
FIG. 2B shows the components utilized in the various epoxy formulations.

A wide variety of epoxy resins containing an epoxide functional group can be reacted with the amine curative, including commercially available novolacs, EPONEX 1510, Araldite, DER 732, EPON 826, and EPON 828. As an example, epoxy/amine thermosets were prepared from the DADBCO isomer mixture or the isolated trans- or cis-isomers and the commercial epoxy resin EPON 828 according to the formulations shown in Table 2 (chemical structures for the components are shown in FIG. 2B). In brief, epoxy and amine curative components were mixed at 1:1 stoichiometry (32 phr) and cured at 150° C. for 1 h. Ethylene dianiline (EDA) was employed in a separate formulation to serve as a control. Unlike DADBCO, EDA was not expected to undergo thermal isomerization. The curing reactions were monitored by DSC and FT-IR spectroscopy. In both cases, curing was moderately faster for the trans- and cis-DADBCO isomers than for the DADBCO mixture or EDA. However, curing appeared to be complete in <30 min in all cases. Thermal characterization of the as-prepared thermoset samples was carried out using thermogravimetric analysis (TGA) and DSC. These thermal properties are summarized in Table 3. The epoxy samples exhibited good thermal stability up to 350° C. under $N_2$ atmosphere and glass transition temperatures ($T_g$) that ranged from approximately 100-160° C. depending on the identity of the curative and the curing method (i.e., cured during fast temperature ramp or isothermal curing at 150° C.). Of note, the $T_g$ of the epoxy cured with cis-DADBCO was 10-30° C. lower than those cured with trans-DADBCO, the DADBCO mixture, or EDA. It could be the case that the additional mobility afforded by the twist-boat to chair isomerization depressed the $T_g$ in the cis-DADBCO sample.

TABLE 2

Epoxy formulations.

| Epoxy | Curative | EEW[a] | AEW[b] | Stoichiometry (epoxide/amine) | Amine wt % | phr[c] |
|---|---|---|---|---|---|---|
| Epon 828 | EDA | 188 | 53 | 1:1 | 22 | 28 |
| Epon 828 | DADBCO (mixed) | 188 | 60 | 1:1 | 24 | 32 |
| Epon 828 | trans-DADBCO | 188 | 60 | 1:1 | 24 | 32 |
| Epon 828 | cis-DADBCO | 188 | 60 | 1:1 | 24 | 32 |

[a]Epoxide equivalent weight = ratio of MW to the number of epoxide functional groups.
[b]Amine equivalent weight = ratio of MW to the number of amine functional groups.
[c]Parts per hundred resin

TABLE 3

Summary of thermal properties of cured epoxies.

| ID | $\Delta H_{cure}$ (J/g)[a] | $T_{g, ramp}$ (°C.)[b] | Cure time @ 150° C. (min)[c] | $T_{g, iso}$ (°C.)[d] | $T_d$ (°C.)[e] | Weight loss (%)[f] |
|---|---|---|---|---|---|---|
| $EF_{control}$ | 453 | 154 | 26 | 163 | 366 | 84.1 |
| $EF_{mixed}$ | 269 | 134 | 21 | 142 | 351 | 80.7 |
| $EF_{trans}$ | 112 | 130 | 15 | 142 | 355 | 83.8 |
| $EF_{cis}$ | 114 | 105 | 10 | 131 | 357 | 83.3 |

[a]Curing enthalpy calculated from the area under the curve of the temperature ramp cure DSC trace.
[b]Calculated via DSC from the first heating cycle of the un-cured sample.
[c]The curing time represents the time at which the derivative of the heat flow vs time curve reached zero in the DSC isothermal curing experiment.
[d]Calculated via DSC from the second heating cycle following isothermal curing at 150° C. for 1 h.
[e]Decomposition temperature represents the onset of the mass loss occurring at ~200° C. for all samples.
[f]Change in sample mass following water loss (measurement range ~150-600° C.).

Figure 6B:
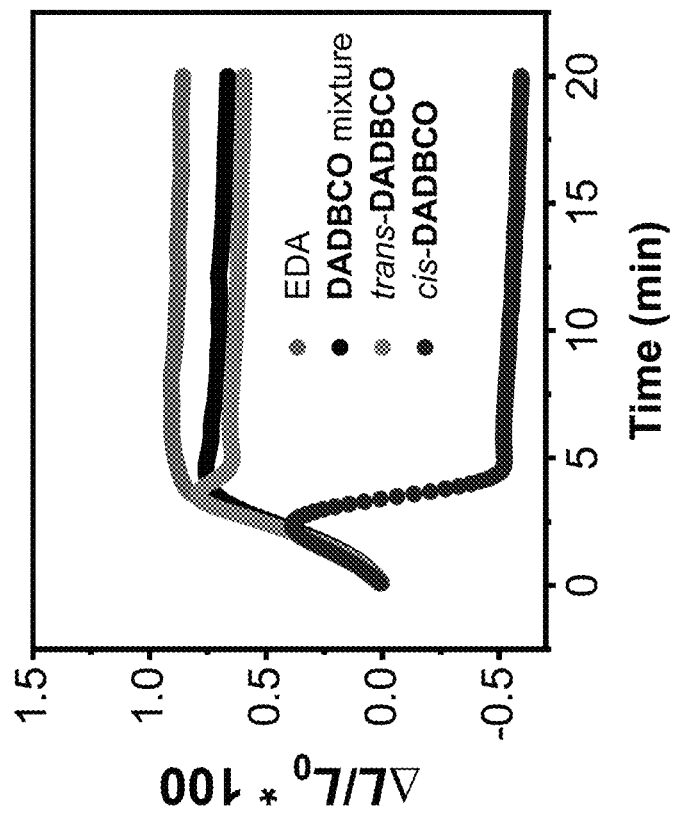
FIG. 6B is a graph of the time spent at 160° C. for the DADBCO- or EDA-cured samples.
Figure 6A:
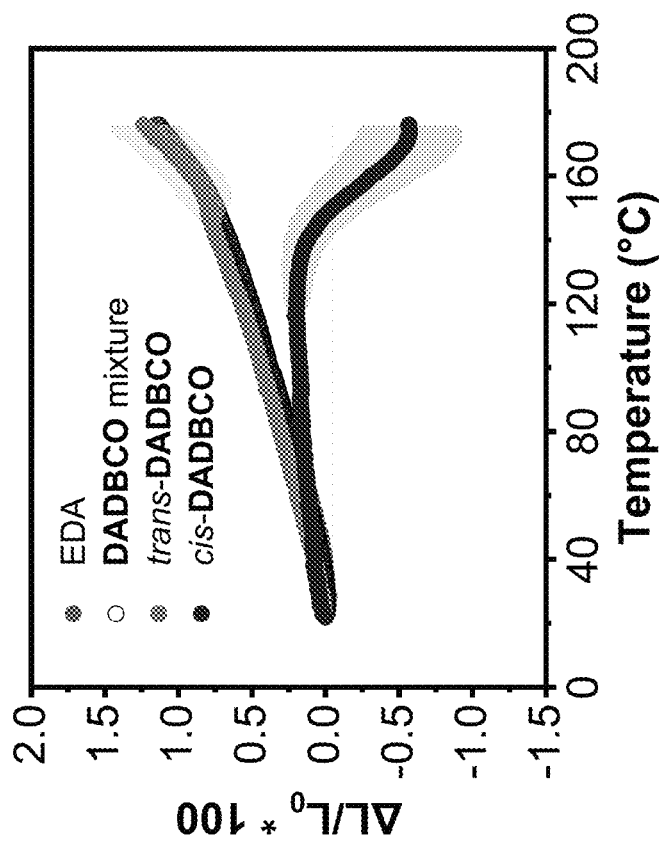
FIG. 6A is a graph of the thermal expansion/contraction ratio of epoxy samples as a function of temperature (25-180° C. at a heating rate of 10° C./min, second heating cycle).

TMA was employed to study the thermal expansion and contraction behavior of the various epoxy samples. Sample length was monitored as a function of either temperature (40-180° C.) or time (at 160° C.). The thermal expansion/contraction ratios as a function of either temperature or time for the various samples are shown in FIGS. 6A and 6B, respectively. As shown in FIG. 6A, a linear increase in sample length is observed for the EDA-cured sample up to 155° C., after which the slope increased. This temperature corresponds to $T_g$ and the associated softening of the material. Similar behavior is observed for the sample cured with the DADBCO isomer mixture. In contrast, a rapid contraction is observed for the trans-DADBCO cured sample above its $T_g$, after which the sample continues to thicken. This behavior is more dramatic for the cis-DADBCO sample, which contracts massively above $T_g$. These observations are also apparent in the kinetic data in FIG. 6B, showing initial expansion and then consistent size for the sample cured with EDA, expansion then slight contraction for those cured with the DADBCO mixture or trans-DADBCO, and slight expansion then massive contraction for the cis-DADBCO sample. This contraction occurs rapidly above $T_g$, after which the material maintains a relatively consistent size. Thus, the twist-boat to chair isomerization does not appear to be kinetically controlled but is instead governed by the twist-boat/chair equilibrium. Indeed, the magnitudes of these contractions trend linearly with the calculated equilibrium constants at 200° C., as shown in Table 1.

Figure 7A:
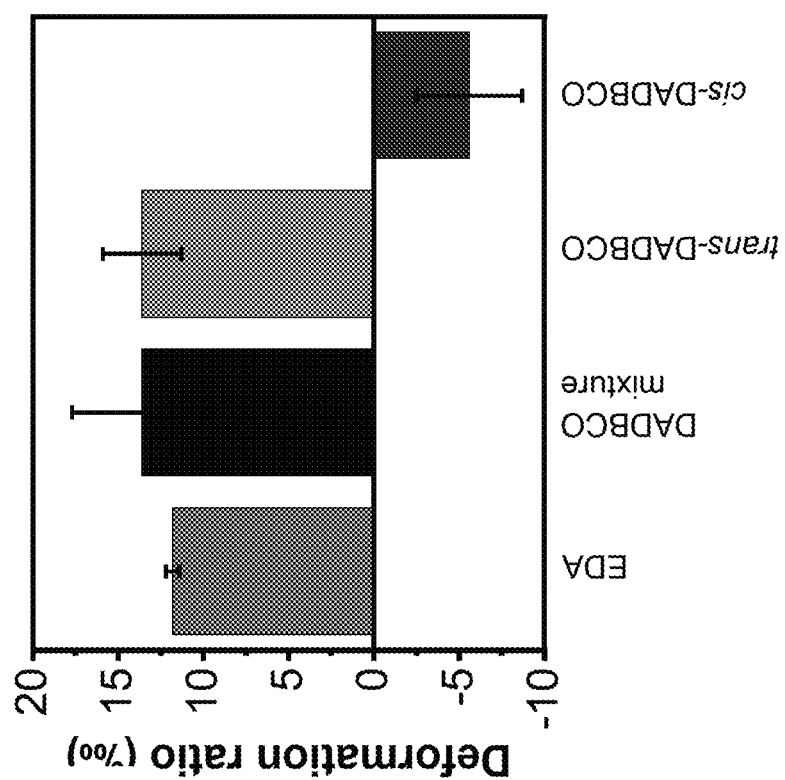
FIGS. 7A and 7B are graphs of calculated CTE and deformation values from data in FIG. 6A.
Figure 7B:
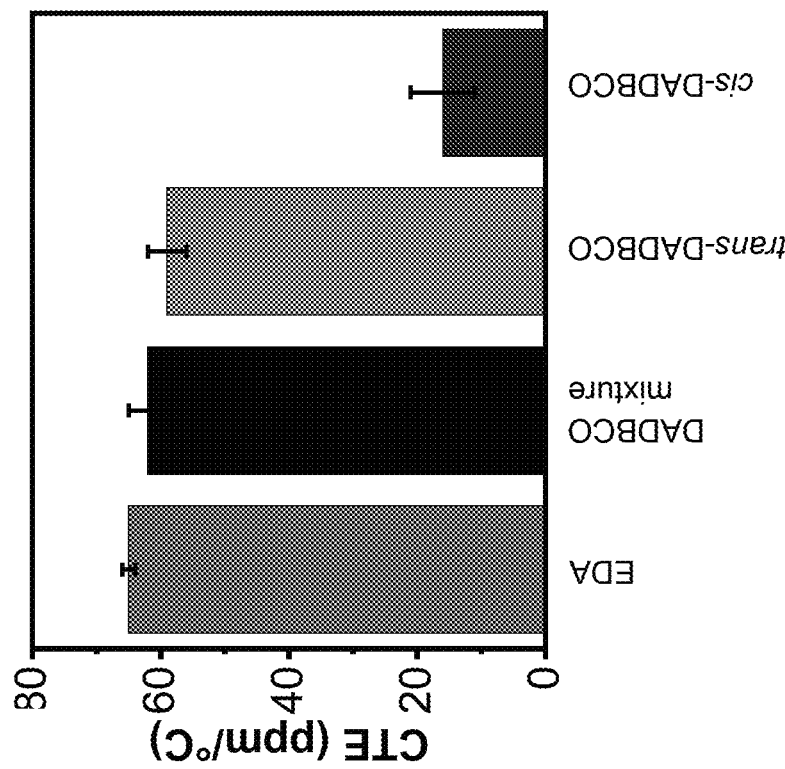

The CTEs for each sample were calculated in the range of 50-100° C. (below $T_g$). As shown in FIG. 7A, the EDA, mixed DADBCO, and trans-DADBCO samples exhibited CTE values typical for epoxy thermosets (ca. 60 ppm/° C.). In contrast, the CTE for the cis-DADBCO sample was 20 ppm/° C. Such a low CTE value is rarely observed in polymer materials. In addition, this sample showed a net contraction across the complete temperature range (20-108° C.) whereas the others expanded upon heating, as shown in FIG. 7B. The temperature at which the slope changed in the plot of expansion/contraction ratio vs. temperature, $T_c$, was observed for each sample. The $T_c$ decreased from 158° C. for the mixed DADBCO sample to 143° C. for the sample cured with cis-DADBCO. A summary of the thermomechanical behavior of the cured epoxies is shown in Table 4. These data trend with the calculated equilibrium constants, shown in Table 1, suggesting a relationship to the position of the twist-boat/chair equilibrium.

TABLE 4

Summary of thermomechanical behavior of cured epoxies.

| | 1st heating cycle | | | 2nd heating cycle | | | | |
|---|---|---|---|---|---|---|---|---|
| Curative | CTE1[a] (ppm/° C.) | CTE2[a] (ppm/° C.) | $T_c^b$ (° C.) | CTE1[a] (ppm/° C.) | CTE2[a] (ppm/° C.) | $T_c^b$ (° C.) | Contraction[c] (%) | Deform[d] (%) |
| EDA | 71 ± 2 | 130 ± 20 | 162 ± 4 | 65 ± 1 | 130 ± 10 | 158 ± 3 | N/A | 11.8 ± 0.4 |
| DADBCO mixture | 58 ± 4 | 110 ± 30 | 157 ± 3 | 62 ± 3 | 140 ± 20 | 158 ± 3 | −0.3 | 13.6 ± 4.1 |
| trans-DADBCO | 64 ± 3 | 160 ± 120 | 134 ± 13 | 59 ± 3 | 170 ± 60 | 149 ± 5 | −2.1 | 13.6 ± 2.3 |
| cis-DADBCO | −2 ± 5 | 340 ± 140 | 139 ± 4 | 16 ± 5 | −250 ± 80 | 143 ± 1 | −9.3 | −5.6 ± 3.1 |

[a]CTE values calculated from the 1st (50-100° C.) and 2nd (150-170° C.) slopes of the various TMA heating curves.
[b]Temperature at which the slope of the TMA curve changes between the reported CTE values.
[c]The maximum contraction of the sample experienced immediately after $T_c$ in the isothermal experiments.
[d]The total change in the sample dimension across the complete temperature range (20-180° C.).

Figure 8:
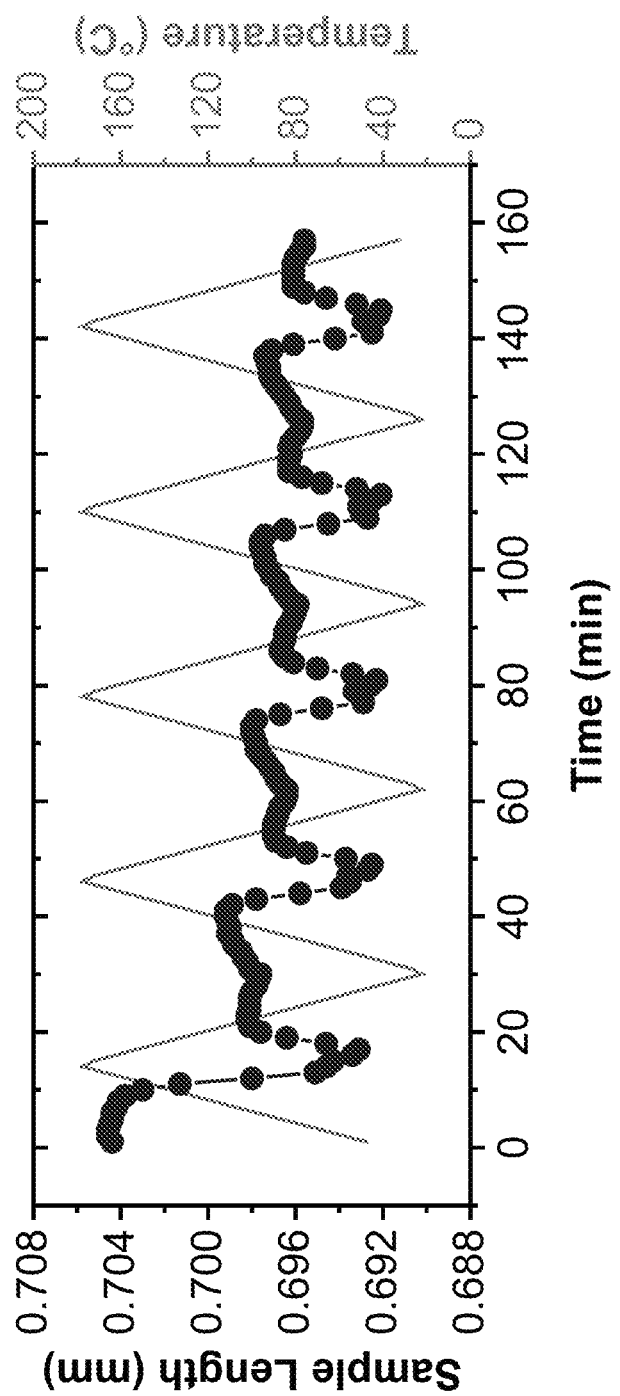
FIG. 8 is a graph showing the reversibility of thermal expansion and contraction for epoxy cured with cis-DADBCO over five heating and cooling cycles. The samples were cycled a rate of 10° C./min.

The reversibility of the thermal contraction behavior was examined. The cis-DADBCO sample was subjected to five heating and cooling cycles from 20-180° C. at 10° C./min. As shown in FIG. 8, sample contraction was observed during the heating ramp of each cycle followed by re-expansion during cooling, demonstrating good reversibility. The magnitude of the length changes associated with expansion/contraction generally decreased with each cycle, perhaps due to thermal re-arrangement and/or relaxation of the epoxy resin constituents. The large initial contraction upon heating could be recovered via physical aging for at least 24 h at room temperature.

Taken together, data from DFT calculations and TMA experiments show that the macroscopic thermal expansion/contraction behavior of the cured epoxy samples depends on the equilibrium of isomerization of the DBCO moieties on the molecular level. In particular, a large shift from positive to negative $\Delta G$ with temperature for cis-DADBCO corresponded to reduced CTE below $T_g$ and a large contraction above $T_g$ in the cured epoxy.

The synthetic approach to reducing CTE can be applied to a variety of thermosetting resins, including but not limited to epoxy resins, acrylates, methacrylates, unsaturated polyesters, vinyl esters, and urethanes, and other crosslinked polymer systems to provide a tunable coefficient of thermal expansion. The curative can comprise any molecule that can undergo a twist boat/chair or cis/trans isomerization which is energetically favored to flip to a secondary conformation at elevated temperatures in which the energetically favorable conformation has a smaller volume than the conformation at room temperature. The curative can be substituted with a variety of reactive groups, including amines, carboxylic acids, alcohols, isocyanates, anhydrides, epoxides, etc.

Figure 9A:
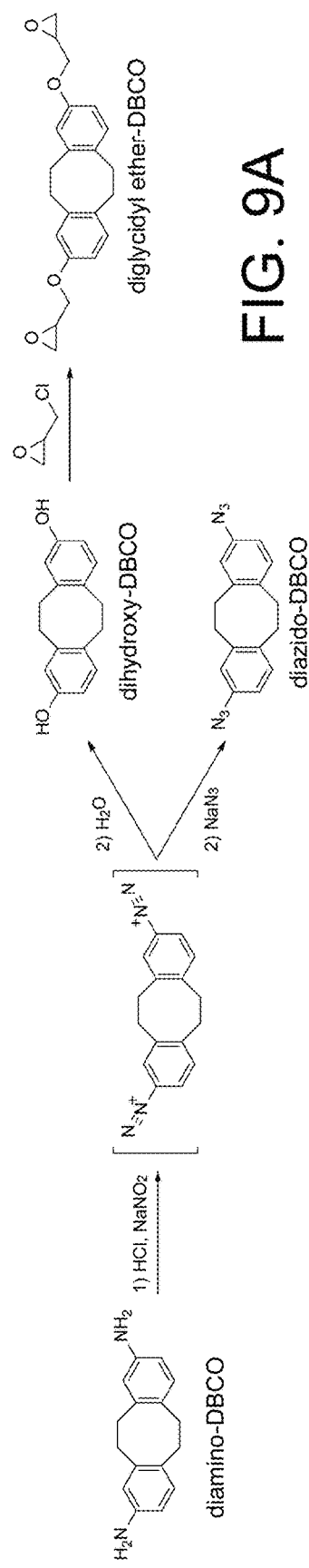
FIG. 9A shows a synthetic route to prepare a diepoxide-dibenzocyclooctane and a diazido-dibenzocyclooctane.
Figure 12A:
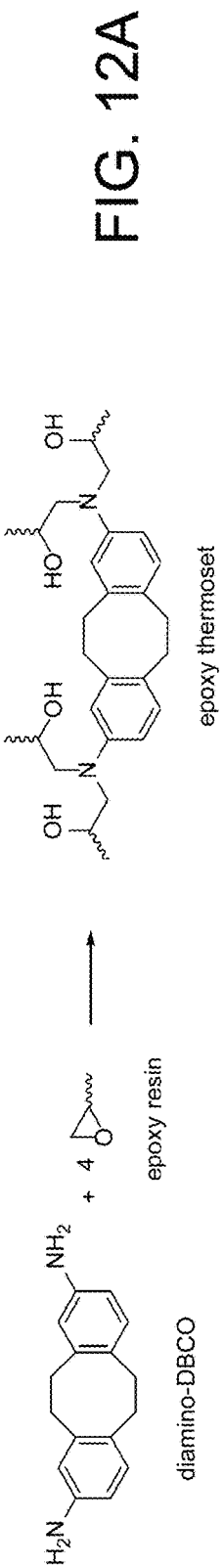
FIG. 12A shows the reaction of a diamino-dibenzocyclooctane curative with an epoxy resin to form an epoxy thermoset.

Crosslinking of an epoxy resin with diamino-dibenzocyclooctane to form an epoxy thermoset is shown in FIG. 12A. The approach can be used with other epoxy curatives that can crosslink with epoxy resins to form thermosets. FIG. 9A shows a synthetic route to prepare diepoxide- and diazido-dibenzocyclooctanes. In this scheme, diamino-dibenzocyclooctane is reacted with sodium nitrite in hydrochloric acid to form a diazo compound in situ. Addition of sodium azide to the diazo compound yields the diazido-dibenzocyclooctane. Addition of water to the diazo compound yields a diphenol. O-Alkylation of the diphenol with epichlorohydrin yields the diglycidyl ether-dibenzocyclooctane.

Figure 9B:
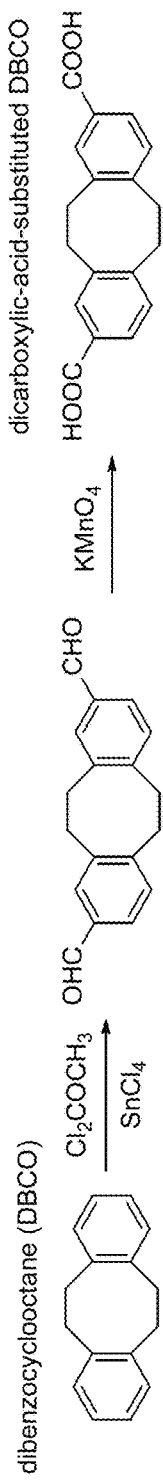
FIG. 9B shows a synthetic route to prepare a dicarboxylic-acid-substituted dibenzocyclooctane and a dianhydride-dibenzocyclooctane.

FIG. 9B shows a synthetic route to prepare dicarboxylic-acid-substituted dibenzocyclooctane and dianhydride-dibenzocyclooctane. Formylation of dibenzocyclooctadiene using dichloromethyl methyl ether and tin (IV) chloride yields a dialdehyde. Many regioisomers of the dialdehyde are possible, but they can be separated with column chromatography. Oxidation of the dialdehyde with potassium permanganate yields the dicarboxylic-acid-substituted dibenzocyclooctane. The dicarboxylic-acid-substituted dibenzocyclooctane can be acylated with chloroacetone to give the dianhydride-dibenzocyclooctane.

Figure 9C:
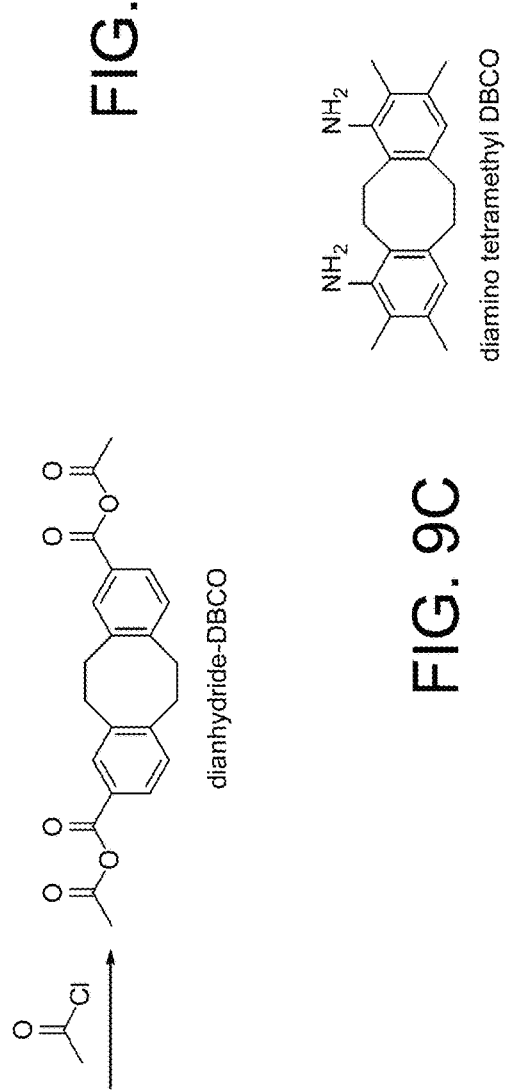
FIG. 9C shows an ortho, ortho-cis-diamino version of tetramethylated dibenzocyclooctane.
Figure 9C:
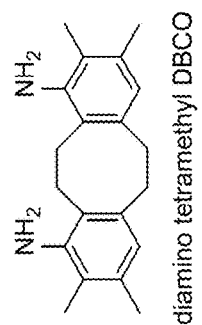

The phenyl rings of a disubstituted dibenzocyclooctane can be further substituted with one or more alkyl groups such that the molecule can still undergo reversible twist-boat to chair isomerization. FIG. 9C shows an exemplary ortho-ortho-cis diamino version of tetramethylated dibenzocyclooctane.

Figure 10A:
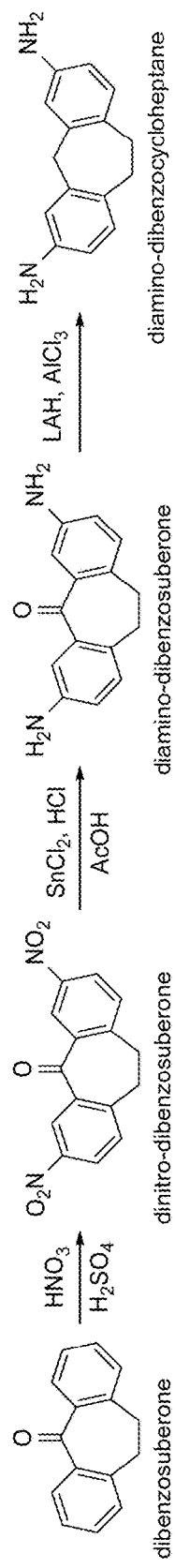
FIG. 10A shows a synthetic route to prepare a diamino-dibenzocycloheptane.

In addition, the approach can be also used with other thermally contractile units that undergo a reversible twist-boat to chair isomerization upon heating accompanied by a change in molecular volume. FIG. 10A shows a synthetic route to prepare a diamino-substituted dibenzocycloheptane. Dibenzosuberone can be nitrated using a mixture of nitric and sulfuric acid to give dinitro-dibenzosuberone as the major regioisomer. The nitro groups on dinitro-dibenzosuberone can be reduced with tin (II) chloride in a hydrochloric acid and acetic acid solvent to yield diamino-dibenzosuberone. The ketone in diamino-dibenzosuberone can be completely reduced to the methylene group using a combination of lithium aluminum hydride and aluminum trichloride in an ethereal solvent to give diamino-dibenzocycloheptane.

Figure 10B:
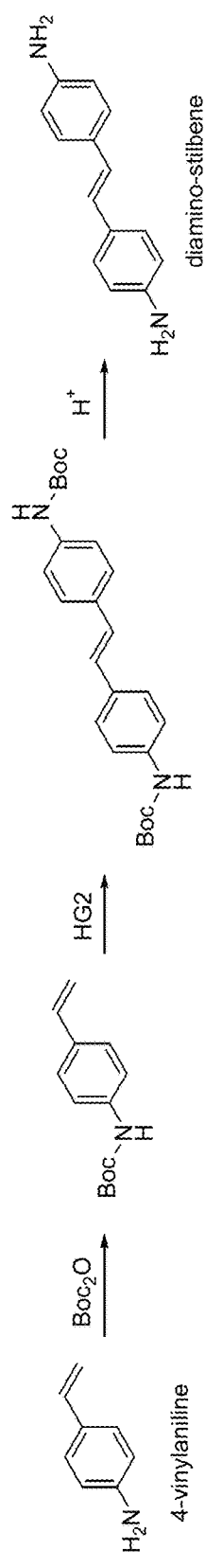
FIG. 10B shows a synthetic route to prepare a diamino-stilbene.
Figure 10C:
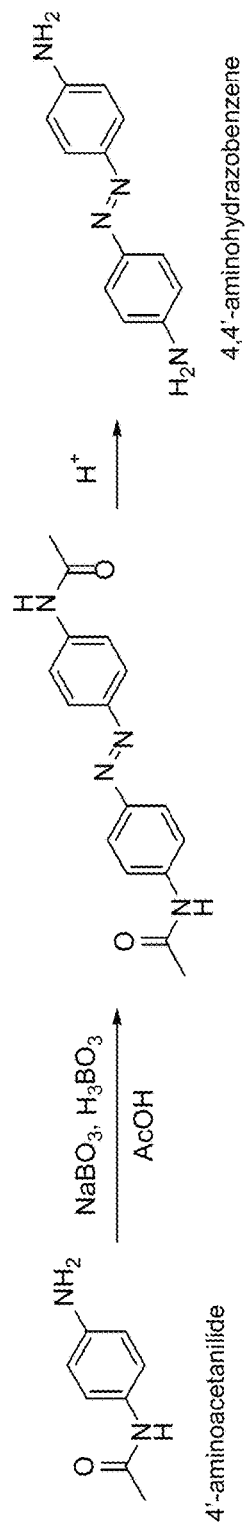
FIG. 10C shows a synthetic route to prepare a diamino-azobenzene.

Other thermally contractile units that can undergo cis/trans isomerization upon heating include stilbene and azobenzene. FIG. 10B shows a synthetic route to prepare diamino-stilbene. 4-vinylaniline can be reacted with di-t-butyl dicarbonate ($Boc_2O$) to give a protected amine. Metastasis of the protected amine using a second-generation Hoveyda-Grubbs (HG2) catalyst yields the predominately trans isomer of the N-protected stilbene. The stilbene can be exposed to acid to remove the t-butyloxycarbonyl (Boc) protecting group and give diamino stilbene. FIG. 10C shows a synthetic route to prepare diamino-azobenzene. 4'-amino-acetanilide can be reacted with boric acid and sodium perborate in acetic acid to yield the substituted azo compound. Addition of acid to the substituted azo compound removes the acyl groups to yield 4,4'-diaminohydrazobenzene.

Figure 11:
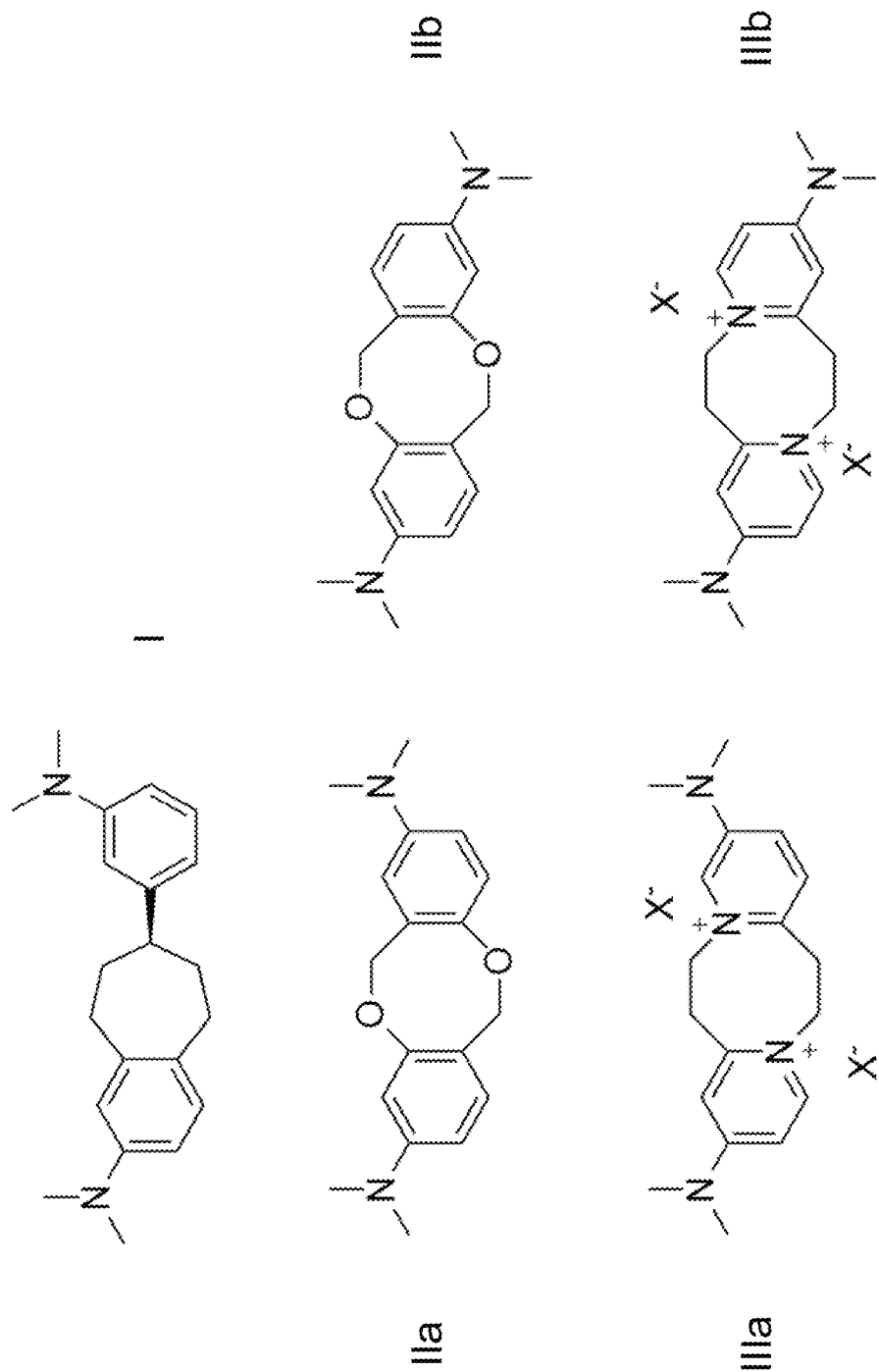
FIG. 11 shows disubstituted thermally contractile units that can undergo twist-boat to chair isomerization.

Still other thermally contractile units that can undergo twist-boat to chair isomerization are shown in FIG. 11. These structures are not limited to the exemplary isomers shown but can include other isomers that exhibit favorable conformal changes upon heating. Further, the tertiary amines shown in these examples can be replaced with any of the other functional groups described above, including carboxylic acids, alcohols, isocyanates, epoxides, anhidrides, etc., to provide bisubstituted structures with different functionalities.

Figure 12B:
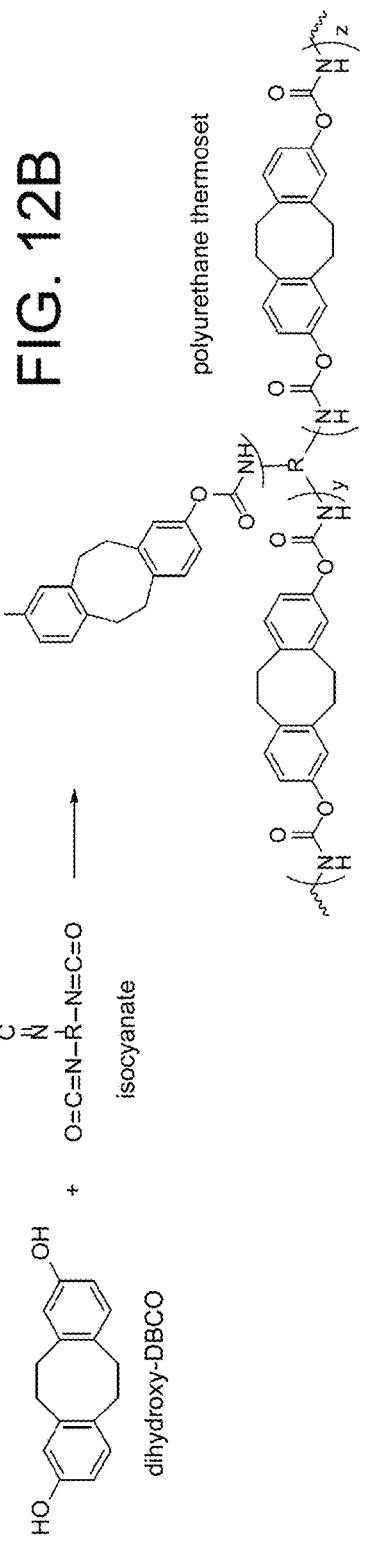
FIG. 12B shows the reaction of dihydroxy-dibenzocyclooctane with an isocyanate to form a polyurethane thermoset.

The synthetic approaches also lend themselves to the creation of DBCO-dialcohol or DBCO-diisocyanate curatives which can reacted into the backbones of polyurethanes. For example, an isocyanate can be crosslinked with dihydroxy-dibenzocyclooctane, as shown in FIG. 12B, or a polyol can be crosslinked with diisocyanate-dibenzocyclooctane to provide a polyurethane thermoset.

Figure 12C:
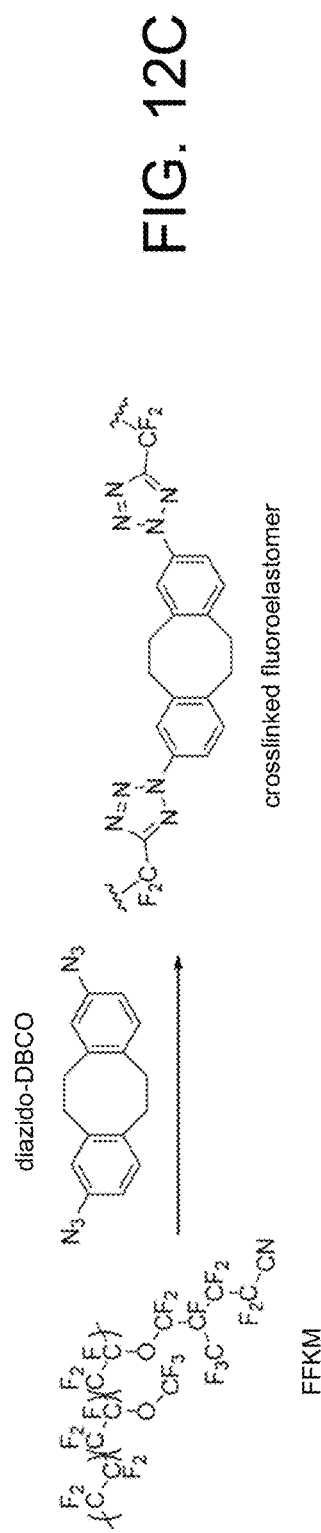
FIG. 12C shows the reaction of a diazido-dibenzocyclooctane curative with the perfluoroelastomer FFKM to form a crosslinked fluoroelastomer.

The approach also can be used to synthesize other crosslinked polymers, such as crosslinked rubbers and fluoroelastomers. For example, the perfluoroelastomer FFKM containing some amount of crosslinkable monomer, such as a cyano-functionalized co-monomer, can be crosslinked with diazido-dibenzocyclooctane to form a crosslinked fluoroelastomer, as shown in FIG. 12C. See G. Tillet et al., *J. Polym. Sci. A Polym. Chem.* 53, 1171 (2015).

The present invention has been described as crosslinked polymers with tunable coefficients of thermal expansion. It will be understood that the above description is merely illustrative of the applications of the principles of the present invention, the scope of which is to be determined by the claims viewed in light of the specification. Other variants and modifications of the invention will be apparent to those of skill in the art.

We claim:

1. An epoxy thermoset comprising an epoxy resin crosslinked with a disubstituted-dibenzocyclooctane curative, wherein the disubstitution consists of a substitution of a functional group on each of the benzene rings.

2. The epoxy thermoset of claim 1, wherein the disubstituted-dibenzocyclooctane curative is selected from the group consisting of diamino-dibenzocyclooctane, diepoxide-dibenzocyclooctane, diazido-dibenzocyclooctane, dihydroxy-dibenzocyclooctane, diisocyanate-dibenzocyclooctane, dicarboxylic acid-substituted-dibenzocyclooctane, or dianhydride-dibenzocyclooctane, and wherein the disubstitution consists of an amino, epoxide, azido, hydroxy, isocyanate, carboxylic acid, or anhydride group substituted on each of the benzene rings, respectively.

3. The epoxy thermoset of claim 1, wherein the disubstituted-dibenzocyclooctane comprises a cis isomer.

* * * * *